US010215769B1

(12) United States Patent
Huettel et al.

(10) Patent No.: US 10,215,769 B1
(45) Date of Patent: Feb. 26, 2019

(54) MULTI-FLUID JET NOZZLE FOR SENSOR CALIBRATION

(71) Applicant: The Florida State University Research Foundation, Inc., Tallahassee, FL (US)

(72) Inventors: Markus H. Huettel, Tallahassee, FL (US); Alireza Merikhi, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 45 days.

(21) Appl. No.: 15/709,875

(22) Filed: Sep. 20, 2017

Related U.S. Application Data

(60) Provisional application No. 62/397,102, filed on Sep. 20, 2016.

(51) Int. Cl.
*B05B 1/14* (2006.01)
*G01N 35/00* (2006.01)

(52) U.S. Cl.
CPC .............................. *G01N 35/00693* (2013.01)

(58) Field of Classification Search
None
See application file for complete search history.

(56) References Cited

U.S. PATENT DOCUMENTS

| | | | |
|---|---|---|---|
| 2,376,413 A | 5/1945 | Babcock | |
| 3,323,682 A | 6/1967 | Creighton, Jr. et al. | |
| 3,467,269 A | 9/1969 | Newton | |
| 4,265,377 A * | 5/1981 | Moen | B05C 5/0279 118/411 |
| 5,096,746 A * | 3/1992 | Strizki | B05B 13/069 118/315 |
| 5,232,739 A * | 8/1993 | Strizki | B05B 13/069 118/317 |
| 5,303,865 A | 4/1994 | Bert | |

(Continued)

OTHER PUBLICATIONS

Fraden, Handbook of Modern Sensors, Physics, Designs, and Applications, Dynamic Characteristics, Springer, 5th Edition Oct. 16, 2015, pp. 1-11 and 51-52.

(Continued)

*Primary Examiner* — Natalie Huls
*Assistant Examiner* — Mohammed E Keramet-Amircolai
(74) *Attorney, Agent, or Firm* — Nicholas Pfeifer; Smith & Hopen, P.A.

(57) ABSTRACT

A device and method for rapid assessment of sensor response times as the sensor is rapidly switched between two or more calibration fluids discharged from a multi-fluid jet nozzle. The novel method includes exposing the sensor to a first calibration fluid and then rapidly exposing it to a second calibration fluid without removing the sensor from the fluid phase. The sensor's output is then assessed to determine its response time. This method is simpler and less expensive than other methods and allows improved precision timing of the change in calibration fluids without changing flow velocity or exposure to other media or viscosities. An embodiment of the novel device is a dual-fluid jet nozzle that ejects two distinct jets of calibration fluid at the same velocity through a single nozzle discharge aperture divided by a sharply-edged boundary wall.

18 Claims, 7 Drawing Sheets

(56) References Cited

U.S. PATENT DOCUMENTS

| | | | |
|---|---|---|---|
| 5,535,950 A | 7/1996 | Barriac et al. | |
| 5,603,453 A | 2/1997 | Weaver et al. | |
| 6,655,606 B2* | 12/2003 | Earl | B05B 1/1663 |
| | | | 239/104 |
| 7,093,777 B2 | 8/2006 | Lan et al. | |
| 7,938,339 B2* | 5/2011 | Robert | A61L 2/22 |
| | | | 239/214.15 |
| 8,444,068 B2 | 5/2013 | Hahn et al. | |
| 8,827,183 B2 | 9/2014 | Jones | |
| 2004/0016773 A1 | 1/2004 | Wagner | |
| 2005/0156061 A1* | 7/2005 | Lan | B05B 1/14 |
| | | | 239/548 |
| 2006/0180232 A1* | 8/2006 | Glewwe | B01F 3/18 |
| | | | 141/2 |
| 2009/0236215 A1* | 9/2009 | Burlica | B01J 19/088 |
| | | | 204/164 |
| 2013/0037628 A1* | 2/2013 | Wurz | B05B 7/0012 |
| | | | 239/418 |
| 2014/0182695 A1* | 7/2014 | Alvi | F15D 1/008 |
| | | | 137/13 |

OTHER PUBLICATIONS

Boon-Brett et al., A comparison of test methods for the measurement of hydrogen sensor response and recovery times, International Journal of Hydrogen Energy, 2010, vol. 35, pp. 7652-7663.

\* cited by examiner

MULTI-FLUID JET NOZZLE FOR SENSOR CALIBRATION

CROSS-REFERENCE TO RELATED APPLICATIONS

This nonprovisional application claims priority to provisional application No. 62/397,102, entitled "MULTI-FLUID JET NOZZLE FOR GENERATING SHARP BOUNDARIES BETWEEN JETS OF FLUIDS," filed Sep. 20, 2016 by the same inventors.

FEDERALLY SPONSORED RESEARCH OR DEVELOPMENT

This invention was made with Government support under Grant No. OCE-1334117 awarded by NSF. The government has certain rights in the invention.

BACKGROUND OF THE INVENTION

1. Field of the Invention

This invention relates, generally, to a multi-fluid jet nozzle. More specifically, the invention relates to a multi-fluid jet nozzle configured to generate a sharp boundary between two or more fluids permitting a decreased transition time between the fluids during sensor evaluation and testing.

2. Brief Description of the Prior Art

Sensors are often used in the engineering, environmental, and medical fields to provide data feedback. The response time of these sensors is often critical for data feedback. For example, sensors measuring fluid characteristics in rapidly changing systems (e.g. bloodstream, photosynthetic reactions, polymerization processes, and combustion processes) must have response times that are several times faster than the rate of change in the system being measured. The need for quick sensor response times is especially essential for the regulation of rapidly changing complex systems, such as combustion engines, to facilitate repeatable feedback loops for the control system.

A sensor's response time, $T_r$, is a central characteristic of a sensor and represents the time the sensor needs to detect and quantify a change in a measured parameter. In any sensor, the sensor output does not change instantly when changes are detected in the parameter being measured. The change in a measured parameter first produces a quantitative change in the sensor, which is then typically translated to a digital or analog signal that can be read by a computer or electronic measuring device. Therefore, response time can also be defined as the time required for a sensor output value to change from the previous output value to the new output value, within a selected tolerance of the true new value, after an abrupt change in the parameter being measured.

Producing controlled abrupt changes in the measured parameter is therefore a prerequisite for the determination of the response time of a sensor. Typically, the sensor must be capable of detecting a predetermined percentage of the change of the parameter being measured (e.g. 60, 70, 95, or 100%), which for practical reasons includes values <100% to reduce total measuring time. The response time is measured from the time the measured parameter changes until the time at which the sensor detects that the predetermined parameter has reached a predetermined percentage of the change.

The abrupt change can be a change in either the positive or negative direction; thus, there are two response times that refer to the sensor response to a positive or negative change in the measured parameter (See e.g. FIG. 1). The comparison and evaluation of the two response times is another critical characteristic of the sensor, e.g. differences in the two response times can cause sensor systems to experience hysteresis effects.

For the selection of the appropriate sensor for an application, the response time of the sensor must be known. Numerous methods have been developed for the determination of sensor response times, and these methods differ according to the parameter being measured. See Fraden, J., 2015. *Handbook of Modern Sensors: Physics, Designs, and Applications*, 5th ed. 2016 Edition 5ed. Springer. For sensors that measure characteristics of fluids (e.g. temperature, salinity, oxygen or carbon dioxide content, and pH), the response time is typically determined by exposing the sensor to two or more calibration fluids that differ in the parameter under consideration. A prerequisite for these measurements is that the time for the sensor to move from one fluid to the next is short compared to the response time of the sensor. See Boon-Brett, L., Black, G., Moretto, P., Bousek, J., 2010. A comparison of test methods for the measurement of hydrogen sensor response and recovery times. International Journal of Hydrogen Energy 35, 7652-7663. In order to keep this time short, the pathway of the sensor between the fluids needs to be minimized.

The separation between the calibration fluids can use physical boundaries, density gradients or flow. While physical boundaries achieve a complete separation of the calibration fluids, they increase the distance and time between the measurements in the two fluids and may include a change of media from gas to fluid. Separation of fluids by density gradients or flow typically generates boundaries where molecular diffusion or turbulence can generate some mixing of the fluids at the interface. This mixing increases the distance between the non-mixed parts of the calibration fluids and thereby the measurement accuracy of the response time. Many sensors (e.g. sensors with membranes through which the target substance has to penetrate to generate a sensor signal) require movement of the measurement fluids, and this flow also leads to variability in the response time when the flow changes.

Accordingly, what is needed is a more efficient and effective device and method for determining the response time of a sensor. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a more efficient and effective device and method for determining the response time of a sensor is now met by a new, useful, and nonobvious invention.

The novel method of calibrating a sensor includes selecting a fluid, a calibration parameter, and a sensor adapted to detect the calibration parameter. The first calibration fluid has a first known value for the calibration parameter. The novel method also includes fluidically coupling a first source of a first calibration fluid to a first jet-guiding tube in a multi-fluid jet nozzle. The first jet-guiding tube converges towards a first discharge outlet in the multi-fluid jet nozzle.

A second source of a second calibration fluid is also fluidically coupled to a second jet-guiding tube in the multi-fluid jet nozzle. The second calibration fluid has a second known value for the calibration parameter and the second jet-guiding tube converges towards the first discharge outlet in the multi-fluid jet nozzle.

The novel method further includes positioning the discharge aperture in the multi-fluid jet nozzle in close proximity to a tip of the sensor with the tip of the sensor in longitudinal alignment with a flow of the first calibration fluid when discharged from the discharging aperture. The first and second calibration fluids are then simultaneously discharged from the first discharge aperture. The first discharge aperture includes a boundary wall extending towards a proximal end of the multi-fluid jet nozzle to maintain separation between the first and second calibration fluids as they are discharged from the first discharge aperture.

After a predetermined time, the multi-fluid jet nozzle is rapidly translated into longitudinal alignment with the second calibration fluid being discharged from the first discharge aperture. The data from the sensor can then be analyzed to determine the response time for the sensor.

In an embodiment, the step of discharging the first and second calibration fluids includes the first and second calibration fluids having the same velocity. An embodiment includes the first and second calibration fluids having a discharge velocity of 30 to 100 cm s$^{-1}$ for the application described in the experimentation section.

In an embodiment, the tip of the sensor is sized to be fully immersed within either the first or second calibration fluids when the first or second calibration fluids are discharged from the discharge aperture. An embodiment includes the sensor tip being within 0.01 to 0.1 cm of the multi-fluid jet nozzle for the application described in the experimentation section.

In an embodiment, the multi-fluid jet nozzle is translated at a speed which enables the sensor to move from the first calibration fluid to the second calibration fluid within a time frame that is no more than 10% of an expected response time of the sensor.

An embodiment may also include the step of selecting a specific multi-fluid jet nozzle, having known dimensions for the jet-guiding tubes and the discharge aperture, based on flow characteristics of the selected fluid. In addition, an embodiment further includes the step of fixing the location of the sensor.

The novel multi-fluid jet nozzle includes a main body having a proximal end and a distal end, with the distal end having a single discharge aperture and the proximal end having a first inlet aperture and a second inlet aperture. The first inlet aperture is laterally spaced from the second inlet aperture along a surface of the proximal end of the main body. A first jet-guiding tube extends between the discharge aperture and the first inlet aperture and a second jet-guiding tube extends between the discharge aperture and the second inlet aperture. The first and second jet-guiding tubes converge towards each other from the inlet apertures towards the discharge aperture.

A boundary wall with a sharp edge divides the discharge aperture into multiple sections. The boundary wall extends from the distal end into contact with the jet-guiding tubes to maintain separation between the first and second jet guiding tubes and creates a joint fluidic jet after fluids from each jet-guiding tube exit the discharge aperture.

Both the first and the second jet-guiding tubes have a constant cross-section extending from the first and second inlet apertures, respectively, to a point at which the jet-guiding tubes reaches the boundary wall.

In an embodiment, the first and second jet-guiding tubes converge away from each other at an angle of 5 degrees or less when moving from the distal end to the proximal end of the nozzle. In an embodiment, the first jet-guiding tube has the same dimensions as the second jet-guiding tube.

An object of the invention is to provide a novel method for determining the response time of a sensor.

It is a further object of the invention to provide a multi-fluid jet nozzle having a single discharge aperture for two or more fluids to create a sharp boundary line between the two or more fluids discharged from the nozzle.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes a device and method for rapid assessment of sensor response times as the sensor is switched rapidly between media. An embodiment of the novel device is a dual-fluid jet nozzle (DFJN) that ejects two jets of fluid (also referred to as "calibration fluid") at the same velocity. The nozzle is configured such that the two jets effectively produce a single jet stream comprising two fluids separated by a sharp boundary. An embodiment of the novel device may be configured to discharge more than two jets of fluid to create a jet stream containing multiple fluids separated by sharp boundaries. The detailed description section, however, will mostly focus on a DFJN in an effort to keep the section concise and comprehensive.

The DFJN is configured to discharge the two calibration fluids at an equal, high-speed velocity (the speed should be proportional to the viscosity of the fluid, i.e. velocities used for liquids will be lower than velocities used for gases). The equal, high-speed discharge of the two calibration fluids minimizes the mixing between the two fluids when said fluids are discharged from the nozzle. The required discharge velocities scale with fluid viscosity and for aqueous solutions range from 10 to 300 cm s$^{-1}$ and for gases from 10 to 300 m s$^{-1}$. This allows large concentration differences (or differences in other fluid properties like temperature or luminescence) over very short horizontal distances (the distance between the jets is horizontal when the DFJN is vertically oriented) and overcomes problems associated with molecular diffusive transport that usually prevents persisting sharp boundaries between two fluids of different concentrations.

For the application described here, the horizontal distance between the centers of the fluid jets is 0.5 cm, and the mixed zone at the interface of the two jets has a maximal thickness of 1 mm at the level of the sensor tip. For applications with gases, this distance between the centers of the jets increases to 1 cm and the mixed zone has a maximal thickness of 2 mm at the level of the sensor tip. The sharp crested boundary wall separating the discharge aperture has an edge that is 10 to 50 µm wide for the application described herein.

Figure 1:
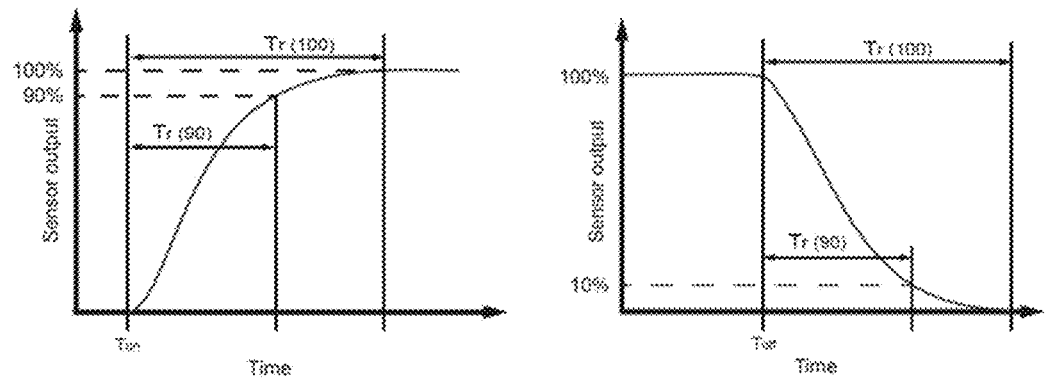
FIG. 1 provides graphs of response times required by a sensor to register 90% (Tr (90)) or 100% (Tr (100)) of a change in the value of a measured parameter after that value increased and decreased. Note that response times as well as the characteristics of the response curve for increasing and decreasing parameter value changes can differ.
Figure 2:
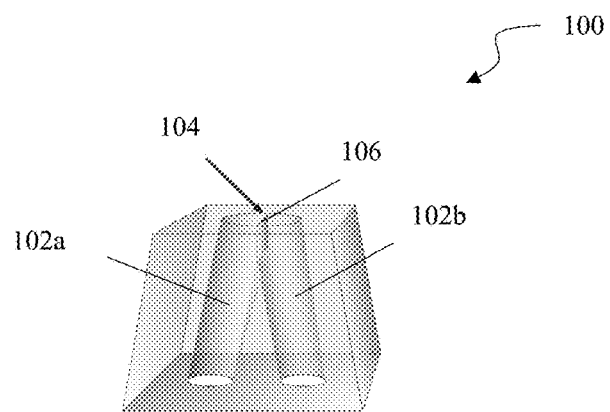
FIG. 2 is a perspective view of an embodiment of the dual fluid jet nozzle.

As shown in FIG. 2, an embodiment of DFJN 100 includes two jet-guiding tubes 102a, 102b converging towards each other as the tubes approach discharge aperture 104. Boundary wall 106 establishes a sharp edge disposed proximate to discharge aperture 104 to effectively divide discharge aperture 104 into two separate discharge apertures. Boundary wall 106 prevents mixture of the two fluidic jet streams prior to exiting nozzle 100 and minimizes the mixture of the two fluids downstream from nozzle 100.

The length of boundary wall 106 is determined by the geometry of the flow. As depicted, boundary wall 106 has a distal end that terminates at the opening of discharge aperture 104. An embodiment may include a boundary wall having a distal end that terminates prior to the distal end of discharge aperture 104 or terminates distally from the distal end of discharge aperture 104.

To maintain a symmetrical, predictable flow profile, the circular cross-sections of jet-guiding tubes 102a, 102b are maintained as long as possible before reaching the point at which the two jets-guiding tubes join, i.e. reach boundary wall 106. In the dual nozzle configuration, the circular cross-section of each jet-guiding tube 102a, 102b is reduced to a partial circular cross-section, or a more oval-shaped cross-section, having a cross-sectional diameter no less than 50% of the respective jet-guiding tube, with the length of the transition between circular and partial circular cross-section depending on the angle between jet-guiding tubes 102a, 102b. For viscous fluids like oils, an angle between the jet-guiding tubes of between 10 and 5 degrees may produce best results, while for aqueous fluids, angles of 5 to 1 degrees are used. For low-viscosity fluids and gases, a parallel orientation of jet-guiding tubes, designed as half-tubes, is used. In a multi jet configuration, the circular cross-sections may be square in the same fashions. The length of non-circular cross-sections is minimized because the corners formed in half-circle or square cross-sections form zones of slow moving fluid that can affect the sharp boundary where the jets meet.

The angle between jet-guiding tubes 102a, 102b in the DFJN and the curvature and dimensions of these tubes depend on the fluids that are used and on the dimensions of the sensor to be tested. The smaller the angle between the two adjacent fluidic jets, the better the sharp interface can develop and this angle will be defined by the boundary wall that separates the two individual fluidic jets. As stated above, the section in which the cross-section becomes non-circular should be minimized. As a result, the angle is a compromise between minimizing the angle and minimizing the length of the non-circular section. Angles are ideally 10 degrees or less.

Similar to non-circular cross-sections, curvatures in the path produce irregularities in the flow. Curvature near the meeting point between the two fluidic jets should thus be avoided. As curvature can reduce the section with a non-circular cross-section of the jets, again a compromise between curvature and the length of the straight sections will produce the best results. As an example, the radius of curvature between the two radii ending at the end of an arc (assumed here to be 3 cm in length) should be no less than 35 cm.

The jet-guiding tubes should have the same diameter so that flow profiles are the same. Ideally all tubes (in multi jet designs) should be of same dimensions to produce flows with similar characteristics. The widths of the jets are commensurate with the width of the sensor tip to allow full immersion of the sensor tip in the jet flows. As a guideline, the widths of the jets should be 10-times the width of the sensor tip diameter for best results. For example, a particular nozzle designed for water jets and an optode micro-sensor with a tip diameter of 200 to 400 μm may include a discharge aperture of 2 to 4 mm in diameter. Larger widths of the fluidic jets increase the required time for the lateral movement of the jets to expose the sensor tip to the full jet flow velocity, thus selecting the lowest nozzle tube diameter for the sensor under consideration will produce best results.

Figure 3A:
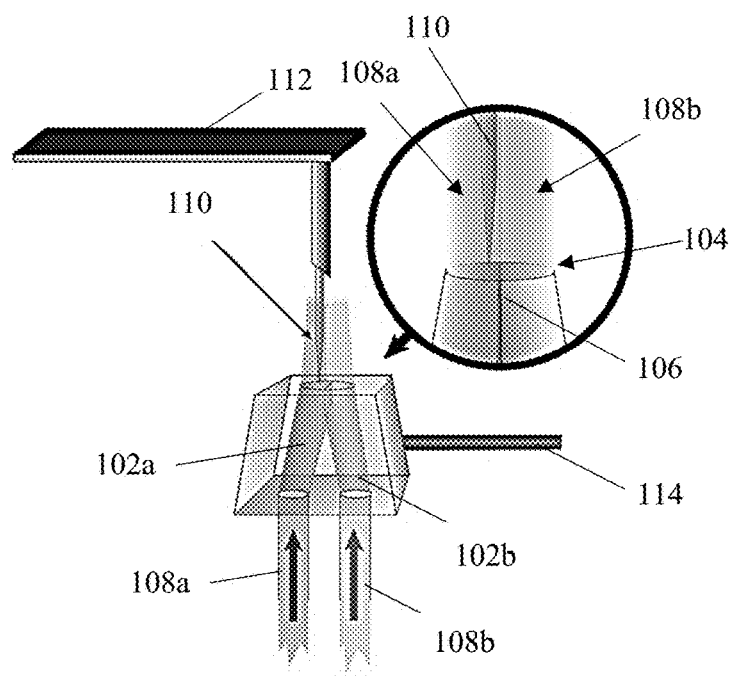
FIG. 3A is a perspective view of an embodiment of the dual fluid jet nozzle (DFJN) illustrating how the two fluid jets are guided to the discharge aperture.
Figure 3B:
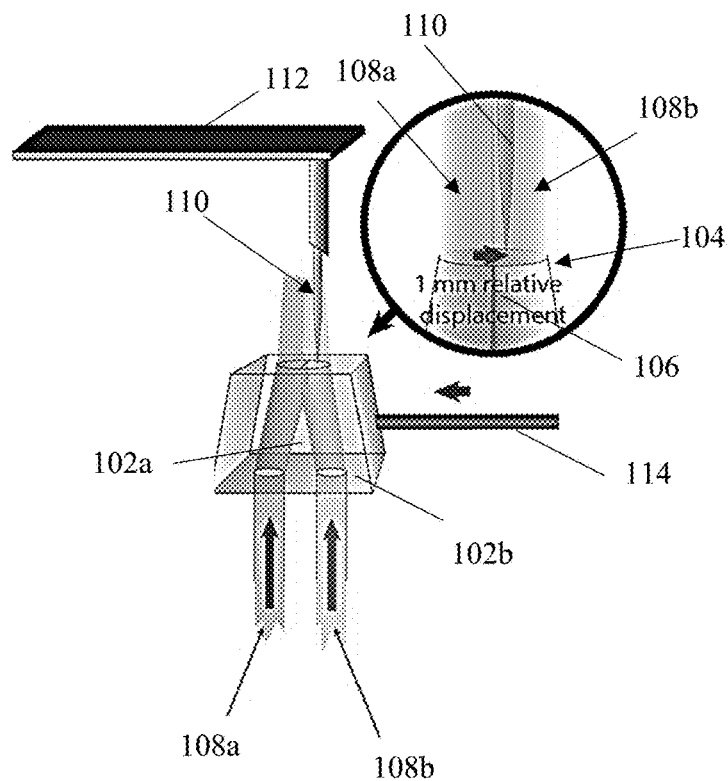
FIG. 3B is a perspective view of an embodiment of the DFJN illustrating how the two fluid jets are guided to the discharge aperture.

Referring now to FIG. 3, an embodiment of the novel method for sensor testing includes simultaneously discharging two calibration fluids 108a, 108b from DFJN 100 with sensor 110 located in close proximity to discharge aperture 104. In an embodiment, sensor 110 is secured to sensor mount 112 and remains fixed while nozzle 100 translates in a perpendicular plane using actuator 114. In an embodiment nozzle 100 may remain stationary while rapidly moving sensor 110 as long as sensor 110 is suitable for abrupt movements. Some sensors, are not adapted for abrupt movement and will record inaccurate data during these rapid movements, so an embodiment employing a fixed sensor may be desirable in such circumstances.

Figure 4A:
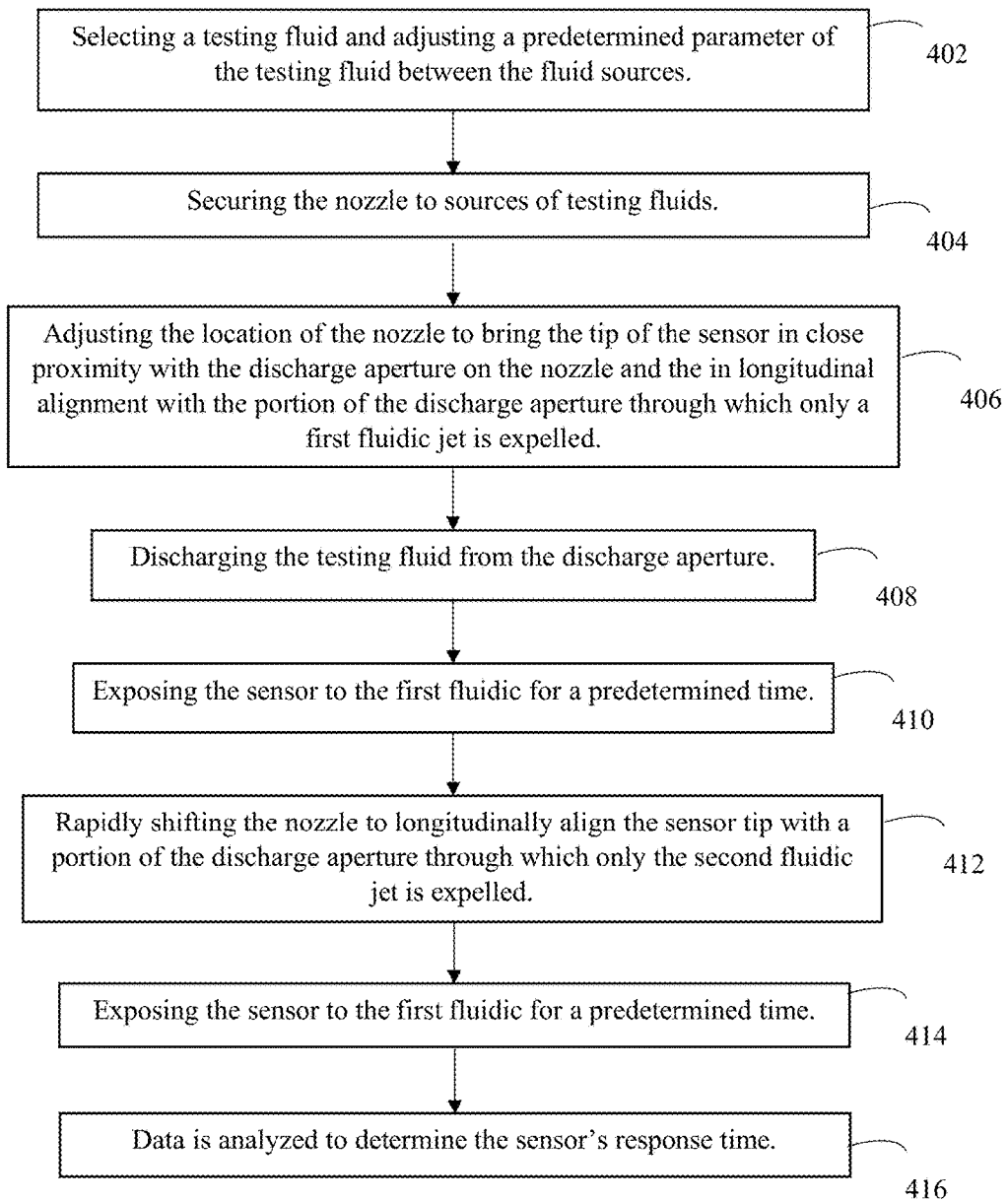
FIG. 4A is an embodiment of the novel method.
Figure 4B:
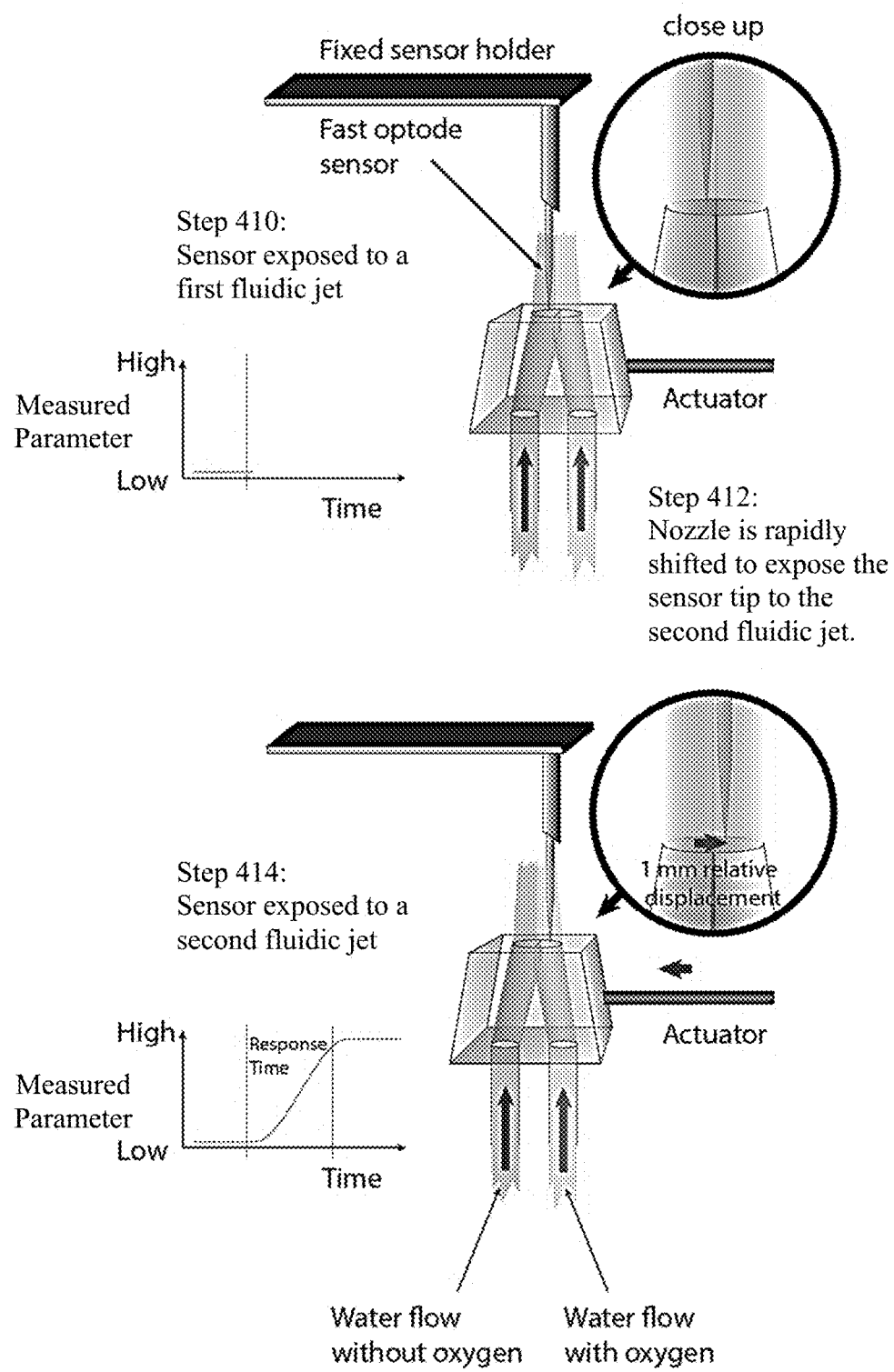
FIG. 4B is a graphic of the method in FIG. 4A.

Referring now to FIG. 4, the novel method is described in greater detail. The exemplary steps and figures correspond to a DFJN, but a nozzle having more than two fluidic jets is considered. The method includes first selecting a calibration fluid and adjusting a predetermined parameter of the calibration fluid between two fluid sources, such that the parameter to be measured by the sensor has different values between the two calibration fluids at step 402. The sources of the calibration fluids, e.g. fluid containers and their respective tubing, are secured to the DFJN at step 404.

At step 406, the DFJN is brought into close proximity with the tip of the sensor and the sensor tip is longitudinally aligned with a portion of the discharge aperture through which only one fluidic jet is expelled. Once the sensor is properly aligned, as depicted in the upper close-up view in FIG. 4B, the calibration fluids are expelled from the discharge aperture in step 408. The sensor records data as depicted in the graph in FIG. 4B for a predetermined time at step 410 and then, at step 412, the nozzle is rapidly shifted to longitudinally align the sensor tip with a portion of the discharge aperture through which only the second fluidic jet is expelled. This configuration is depicted in the bottom half of FIG. 4B and also in FIG. 3B.

The sensor remains exposed to the second fluidic jet for a predetermined time at step 414 and then the data is analyzed to determine the response time of the sensor at step 416.

Testing Results

The method was tested with an optode micro-sensor measuring oxygen content in water. For the application with the optode micro-sensor, the tip of the sensor was placed with a micromanipulator 200 μm above the nozzle blade. The close proximity of the sensor to the nozzle eliminates the effect of diffusion between the two fluid jets. The stationary sensor tip was exposed to a first calibration fluid for 1000 ms and then the nozzle was rapidly moved to expose the sensor to the second calibration fluid for 1000 ms. By moving the DFJN and combined jet rapidly past the sensor tip, the tip was transitioned between the two calibration fluids within microseconds, without removing the sensor from the fluid flow and without altering the flow velocity of the calibration fluids at the measuring locations.

The prototype of the DFJN that was tested was designed for the calibration of microsensors and thus was manufactured with jet-guiding tubes having a diameter of 5 mm, which reduced to a diameter of 4.5 mm at the point where the jet-guiding tubes reach the boundary wall. The tubes merged at an angle of 5 degrees, and a sharp edge formed the boundary wall where the two jet-guiding tubes met. The crest of that edge was less than 50 μm wide in order to reduce turbulence to a minimum.

The 5-degree approach angle of the two jet-guiding tubes is considered a maximum. Larger angles will increase the mixing between the two water jets. Smaller angles between the jet-guiding tubes will improve the performance of the DFJN by further reducing mixing between the two emerging fluid jets. Such smaller angles would be used when using the DFJN for low-viscosity fluids. For gases, parallel tubes, separated by a thin wall will produce best results as the pressurized gas will expand laterally faster than a more viscous fluid. The diameter of the tubes must be small enough to allow the sensor to reach the peaks of the parabolic flow profiles of the fluids emerging the tubes.

The test system included a stationary sensor and a mobile nozzle reliant on an actuator. The lateral movement of the nozzle was achieved by an electromagnetic actuator having a maximum displacement velocity of 1 m/s or 1 mm/ms. For the response time determination, the nozzle for the water jets needed to be moved laterally by 5 mm, which was accomplished in 5 ms. For oxygen optodes with response times of approximately 500 ms, this error is ~1%.

It is critical that time to laterally move the sensor between the calibration fluids is very short compared to the response time of the sensor in order to keep the measuring error minimal, e.g. the time required to change the fluid exposure of the sensor should be less than 10% of the response time of the sensor. The numerical values are dependent on the setup, type of fluid, nozzle dimensions, and sensor type. The speed of lateral movement is also dependent on the diameter of the jets. In the micro optode application, the sensor tip was moved through the radius of the jet in about 2 ms. If the jet is 4 mm in diameter, radius is 2 mm, the speed is 2 mm/2 ms or 1 mm/ms, or, 1 m/s. The prototype setup had smaller diameters and worked with 0.2 m/s. For typical flow diameters of 1 to 5 mm diameter (micro-sensor testing), a range of 0.1 to 1 m/s would be reasonable.

Figure 5A:
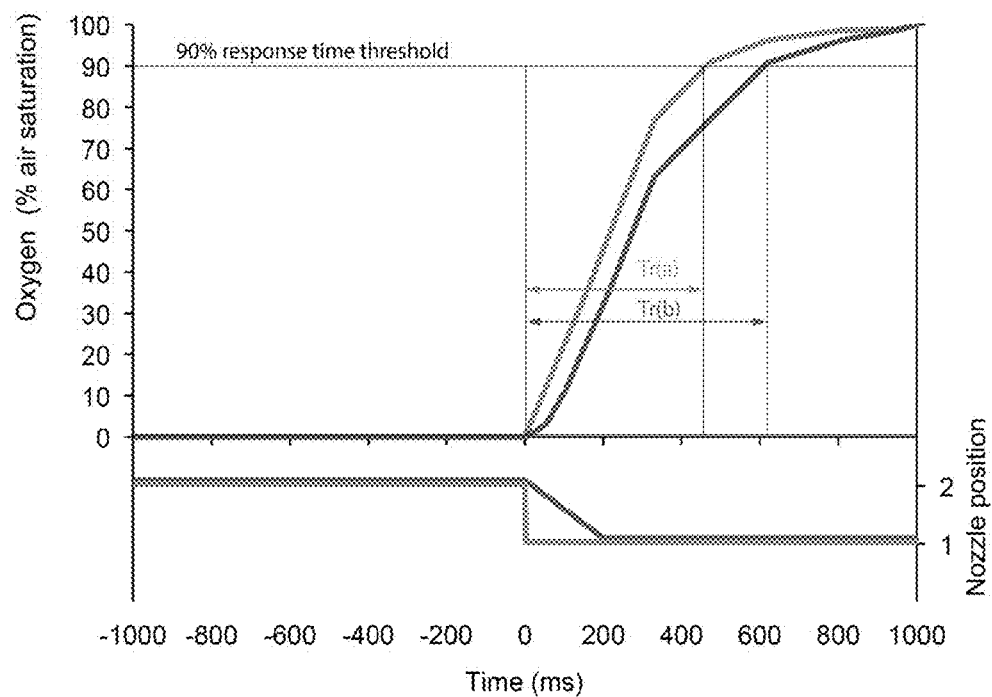
FIG. 5A provides a comparison of the response times (Tr (a) vs. Tr (b), 90% response time threshold) of an oxygen micro-sensor measured in a setup with the DFJN that can switch fluids within 5 ms (light grey curves), and a setup allowing switching calibration fluids within 200 ms (dark grey curves).
Figure 5B:
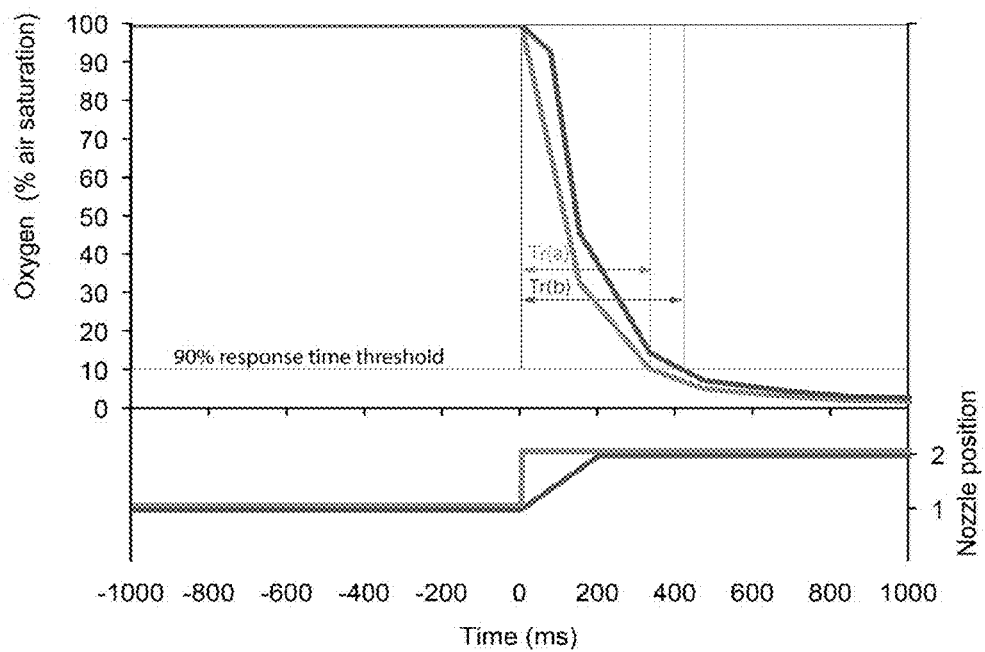
FIG. 5B provides a comparison of the response times (Tr (a) vs. Tr (b), 90% response time threshold) of an oxygen micro-sensor measured in a setup with the DFJN that can switch fluids within 5 ms (light grey curves), and a setup allowing switching calibration fluids within 200 ms (dark grey curves).

The data presented in FIG. 5 demonstrate the error in response time determination caused by switching between calibration fluids over a time period of 200 ms. The two graphs provide a comparison of the response times (Tr (a)

(fast) vs. Tr (b) (slow), 90% response time threshold) of an oxygen micro-sensor measured in a setup with the DFJN that can switch fluids within 5 ms (light grey curves), and a setup allowing switching calibration fluids within 200 ms (dark grey curves). Slower switching (lower curves, right Y-axes) caused an alteration of the sensor response curves as well as an increase in the measured response times (Tr (b)), for both, increased oxygen (left graph) and decreased oxygen (right graph) in the second calibration fluid. In this case, the slower translation increased the response times by 24% and 18%, respectively.

In the above study, the nozzle operation was controlled by a computer that switched the electromagnetic actuators and monitored the movement via displacement sensors (e.g. potentiometric sensors) attached to the piston in the actuators. To assess the exact time that the sensor tip moved from one calibration fluid into the next, an optical fiber was attached to the sensor tip (the fiber is thinner than the sensor tip) that reads the stain of the water jets (inert dyes added to calibration fluids). Because this optical measurement is faster than the oxygen measurement, reference data can be generated even though this measurement also has a small response time delay (~1-50 ms) that varies with the spectrometer used for the fiber readout.

Figure 6A:
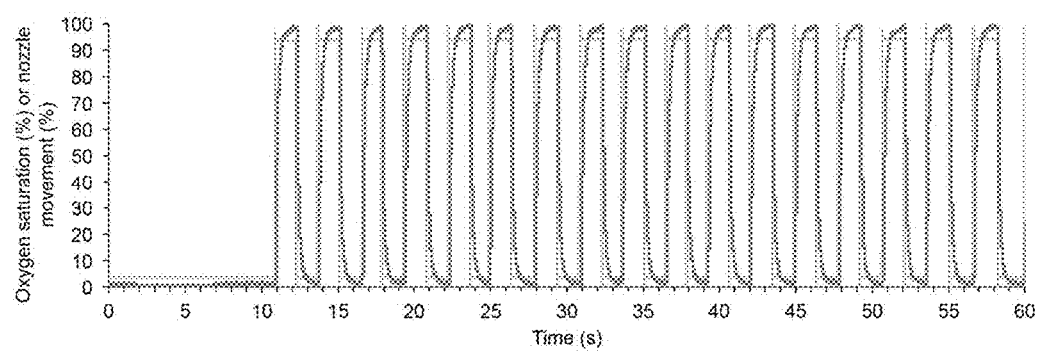
FIG. 6A is a graph of response times measured for the high-speed oxygen fiber sensor using the DFJN where repeated measurements were taken for calibration fluids with 100% and 0% oxygen air saturation. The dark grey line represents the oxygen signal and the light grey line is the signal of the distance sensor.
Figure 6B:
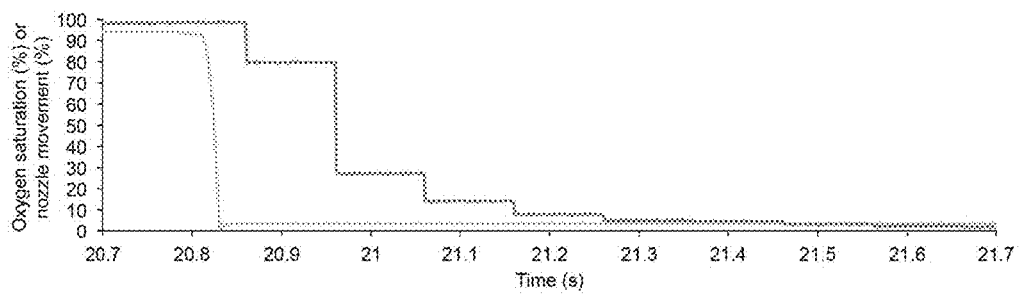
FIG. 6B is a graph of the response of the sensor when measuring the change in oxygen air saturation from 100% to 0%. The dark grey line represents the oxygen signal and the light grey line is the signal of the distance sensor.

The DFJN was also used to measure response times of an oxygen fiber sensor system with ultra-high-speed (UHS) and high-speed (HS) fiber oxygen sensors. The response times for UHS sensors ranged from 150 ms to 250 ms, and ranged from 360 to 600 ms for HS sensors (Table 1). The direction of the oxygen change (0→100%, 100-→0%) had no influence on the response times of the sensors. The measured response times (FIG. 6) had a standard deviation ranging from 4 to 75%, which can be attributed to the variation in the fluorescence signal of the oxygen fiber sensors and the averaging period of ~100 ms that the oxygen sensor electronic uses to produce an output signal (FIG. 6). The lever moving the DFJN was connected to an analog linear position sensor that continuously provided position information to the data logger that collected the oxygen and position information at a frequency of 900 Hz. At the selected moving speed of the DFJN, the full path of the DFJN was completed after 18 ms (SD=2 ms) and the sensor was exposed to the new oxygen concentration in the fluid after 9 ms (SD=1 ms). The moving velocity of the DFJN can be increased for sensors with faster response times. See Table 1. Response times of the ultra-high-speed (UHS) and high-speed (HS) fiber oxygen sensors measured using the dual jet nozzle flow switch.

TABLE 1

Fast fiber oxygen sensor response times (90% threshold)

| | 100% -> 0% | | 0% -> 100% | |
|---|---|---|---|---|
| Sensor # | AV (ms) | SD (ms) | AV (ms) | SD (ms) |
| 1 OXR430-UHS | 150 | 32 | 145 | 25 |
| 2 OXR430-UHS | 236 | 84 | 237 | 130 |
| 3 OXR430-UHS | 250 | 86 | 242 | 66 |
| 4 OXR430-HS | 345 | 26 | 382 | 16 |
| 5 OXR430-HS | 368 | 148 | 363 | 169 |
| 6 OXR430-HS | 382 | 107 | 331 | 249 |
| 7 OXR430-HS | 592 | 159 | 283 | 298 |

Figure 6C:
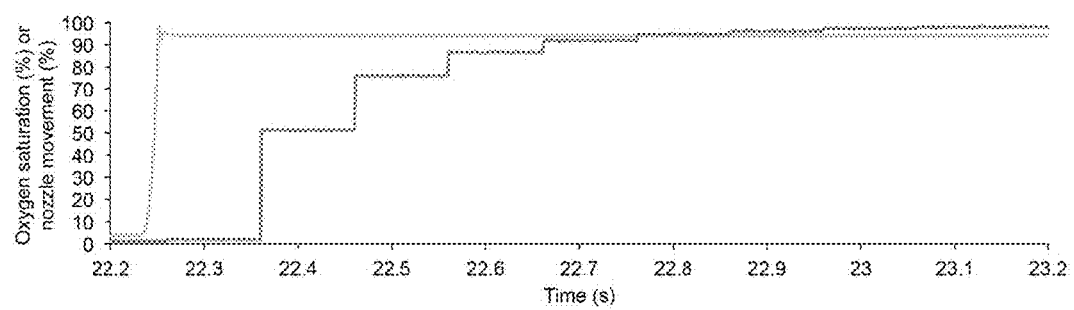
FIG. 6C is a graph of the response of the sensor when measuring the change in oxygen air saturation from 0% to 100%. The dark grey line represents the oxygen signal and the light grey line is the signal of the distance sensor.

The fast movement and inertia caused a small temporal bending of the metal rod holding the nozzle when it reached the end points of the movement, which is reflected in the small overshoot peaks in the light grey distance sensor signal seen at ~130 ms (FIG. 6B) and ~50 ms (FIG. 6C). These peaks were used as the starting time points for the response time measurements. The 900 Hz recordings reveal the ~100 ms integration intervals of the electronics that converted the oxygen fiber fluorescence signal into a voltage that could be recorded by the data logger.

Additional Applications of DFJN

The DFJN also offers applications that are not linked to sensor testing. The rapid switching of fluids with different characteristics could be used in medical research to investigate the responses of biological and chemical systems, e.g. the responses of living tissue cells to abrupt changes in oxygen supply (as caused by injuries), the response of eyes to abrupt changes in the quality of air flow, the testing of sensory cells in the skin to rapid changes of temperature, or the response of enzyme systems to application of pharmaceuticals.

In the chemical field, the DFJN could be useful for the investigation of reaction rates of redox systems (e.g. in corrosion research) or polymer research (e.g. assessment of polymerization rates). The DFJN could improve the quantification of chemical reaction rates similar to the improvement of the response time determination explained in FIG. 4.

In electronic engineering, the DFJN can improve the testing of integrated circuits to sudden changes in temperature, and in mechanical engineering, it could allow assessing and fine-tuning the responsiveness of combustion engines to changes in fuel flow. In airplane, space science and military research there are a vast number of materials, instruments and electronic parts that need to withstand extreme changes in temperature, moisture, oxygen concentration, pressure without failing and therefore need to undergo a large number of stress tests that could be supported by the DFJN technology.

The foregoing are only a few examples of a large spectrum of applications that depend on a quasi-instant change in the micro-environment as facilitated by the DFJN technique to investigate, test, quantify and develop processes, new substances or new devices. For the applications listed above, it is conceivable that the exposure of the biological/chemical/electronic/mechanical system under consideration to a number of different fluids or gases is desirable, in which case a multi-fluid jet nozzle could be used that could operate e.g. in a rotating movement to expose the system to several different fluids or gases. Similarly, this goal could be achieved by installing a fluid switch in the supply lines for the jets that allows changing the fluid reservoirs feeding the nozzle streams. The multiple fluid jet nozzle concept can be used to produce jets containing multiple different fluids separated by sharp boundaries, e.g. a square jet formed by four square jets with one corner of each jet reaching the center of the combined jet. The sensor placed in the center of the combined jet can be moved rapidly between four different fluids by small two-dimensional movements.

Glossary of Claim Terms

Calibration Parameter: is a property, characteristic, or attribute of a fluid.

Fluid: is a substance that can flow, such as a liquid or gas.

Sensor: is a device adapted to measure a certain parameter of a fluid.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of calibrating a sensor, comprising:
   selecting a fluid, a calibration parameter, and a sensor adapted to detect the calibration parameter;
   fluidically coupling a first source of a first calibration fluid to a first jet-guiding tube in a multi-fluid jet nozzle, wherein the first calibration fluid has a first known value for the calibration parameter and the first jet-guiding tube converges towards a first discharge outlet in the multi-fluid jet nozzle;
   fluidically coupling a second source of a second calibration fluid to a second jet-guiding tube in the multi-fluid jet nozzle, wherein the second calibration fluid has a second known value for the calibration parameter and the second jet-guiding tube converges towards the first discharge outlet in the multi-fluid jet nozzle;
   positioning the first discharge aperture in the multi-fluid jet nozzle in close proximity to a tip of the sensor with the tip of the sensor in longitudinal alignment with a flow of the first calibration fluid when discharged from the first discharge aperture;
   simultaneously discharging the first and second calibration fluids from the first discharge aperture, wherein the first discharge aperture includes a boundary wall extending towards a proximal end of the multi-fluid jet nozzle to maintain separation between the first and second calibration fluids as they are discharged from the first discharge aperture;
   after a first predetermined time, rapidly translating the multi-fluid jet nozzle into longitudinal alignment with the second calibration fluid being discharged from the first discharge aperture; and
   analyzing data recorded by the sensor and determining a response time for the sensor.

2. The method of claim 1, wherein the step of discharging the first and second calibration fluids includes the first and second calibration fluids having the same velocity.

3. The method of claim 1, wherein the step of discharging the first and second calibration fluids includes the first and second calibration fluids having a discharge velocity between 30 to 100 cm s$^{-1}$.

4. The method of claim 1, wherein the tip of the sensor is sized to be fully immersed within either the first or second calibration fluids when the first or second calibration fluids are discharged from the first discharge aperture.

5. The method of claim 1, wherein the step of positioning the first discharge aperture in the multi-fluid jet nozzle in close proximity to the tip of the sensor includes the sensor tip being within 0.05 cm of the multi-fluid jet nozzle.

6. The method of claim 1, wherein the step of rapidly translating the multi-fluid jet nozzle into longitudinal alignment with the second calibration fluid includes translating the multi-fluid jet nozzle at a speed which enables the sensor to move from the first calibration fluid to the second calibration fluid within a time frame that is no more than 10% of an expected response time of the sensor.

7. The method of claim 1, further including the step of selecting a specific multi-fluid jet nozzle, having known dimensions for the jet-guiding tubes and the first discharge aperture, based on flow characteristics of the selected fluid.

8. The method of claim 1, further including fixing the location of the sensor.

9. A multi-fluid jet nozzle, comprising:
   a main body having a proximal end and a distal end, the distal end having a first discharge aperture, and the proximal end having a first inlet aperture and a second inlet aperture, wherein the first inlet aperture is laterally spaced from the second inlet aperture along a surface of the proximal end of the main body;
   a first jet-guiding tube extending between the first discharge aperture and the first inlet aperture;
   a second jet-guiding tube extending between the first discharge aperture and the second inlet aperture;
   the first and second jet-guiding tubes converging towards each other from the inlet apertures towards the first discharge aperture; and
   a boundary wall with a sharp edge around 0.05 mm in width dividing the first discharge aperture into multiple sections, the boundary wall extending into contact with the jet-guiding tubes to maintain separation between the first and second jet guiding tubes and creates a joint fluidic jet after fluids from each jet-guiding tube exit the first discharge aperture;
   the second jet-guiding tube having a constant cross-section extending from the second inlet aperture to a point at which the second jet-guiding tube reaches the boundary wall; and
   the first jet-guiding tube having a constant cross-section extending from the first inlet aperture to a point at which the first jet-guiding tube reaches the boundary wall.

10. The nozzle of claim 9, wherein the first and second jet-guiding tube converge away from each other at an angle of 5 degrees or less when moving from the distal end to the proximal end of the nozzle.

11. The nozzle of claim 9, wherein the first jet-guiding tube has the same dimensions as the second jet-guiding tube.

12. A method of calibrating a sensor, comprising:
   selecting a fluid, a calibration parameter, and a sensor adapted to detect the calibration parameter;
   securing the sensor at a fixed location in close proximity to a multi-fluid jet nozzle, wherein the multi-fluid jet nozzle includes:
      a first jet-guiding tube and a second jet-guiding tubes with each tube converging towards each other from a proximal end of the multi-fluid jet nozzle to a distal end of the multi-fluid jet nozzle;
      a first discharge aperture at the distal end of the multi-fluid jet nozzle; and
      a boundary wall extending towards the proximal end of the multi-fluid jet nozzle to maintain separation between the first and second calibration fluids when they are discharged from the first discharge aperture;
   fluidically coupling a first source of a first calibration fluid to the first jet-guiding tube, wherein the first calibration fluid has a first known value for the calibration parameter;

fluidically coupling a second source of a second calibration fluid to the second jet-guiding tube, wherein the second calibration fluid has a second known value for the calibration parameter;

moving the first discharge aperture into a position in which a tip of the sensor is in longitudinal alignment with a flow of the first calibration fluid when discharged from the first discharging aperture;

simultaneously discharging the first and second calibration fluids from the first discharge aperture;

after a predetermined time, rapidly translating the multi-fluid jet nozzle into longitudinal alignment with the second calibration fluid being discharged from the first discharge aperture; and analyzing data recorded by the sensor and determining a response time for the sensor.

13. The method of claim 12, wherein the step of discharging the first and second calibration fluids includes the first and second calibration fluids having the same velocity.

14. The method of claim 12, wherein the step of discharging the first and second calibration fluids includes the first and second calibration fluids having a discharge velocity of 35 cm s$^{-1}$.

15. The method of claim 12, wherein the tip of the sensor is sized to be fully immersed within either the first or second calibration fluids when the first or second calibration fluids are discharged from the first discharge aperture.

16. The method of claim 12, wherein the step of positioning the first discharge aperture in the multi-fluid jet nozzle in close proximity to the tip of the sensor includes the sensor tip being within 0.05 cm of the multi-fluid jet nozzle.

17. The method of claim 12, wherein the step of rapidly translating the multi-fluid jet nozzle into longitudinal alignment with the second calibration fluid includes translating the multi-fluid jet nozzle at a speed which enables the sensor to move from the first calibration fluid to the second calibration fluid within a time frame that is no more than 10% of a predicted response time of the sensor.

18. The method of claim 12, further including the step of selecting a specific multifluid jet nozzle, having known dimensions for the jet-guiding tubes and the first discharge aperture, based on flow characteristics of the selected fluid.

* * * * *